United States Patent [19]
Giaever

[11] 3,960,490
[45] June 1, 1976

[54] METHOD AND APPARATUS FOR DETECTING IMMUNOLOGIC REACTIONS BY DIFFUSION IN GEL

[75] Inventor: Ivar Giaever, Schenectady, N.Y.

[73] Assignee: General Electric Company, Schenectady, N.Y.

[22] Filed: Apr. 1, 1974

[21] Appl. No.: 457,093

[52] U.S. Cl. ............................ 23/230 B; 23/253 R; 23/259; 23/292; 195/103.5 R; 424/12
[51] Int. Cl.² ................. G01N 33/16; G01N 31/02; C12K 1/00
[58] Field of Search ...................... 23/230 B, 253 R; 195/103.5 R; 424/12

[56] References Cited
UNITED STATES PATENTS

| | | | |
|---|---|---|---|
| 3,389,966 | 6/1968 | Saravis | 424/12 X |
| 3,390,962 | 7/1968 | Goldsmith | 424/12 X |
| 3,645,687 | 2/1972 | Nerenberg | 23/230 B X |
| 3,674,438 | 7/1972 | Shen | 23/230 B X |
| 3,692,491 | 9/1972 | Trentelman | 23/230 B X |
| 3,709,661 | 1/1973 | Hubscher | 23/230 B |
| 3,718,436 | 2/1973 | Ushakoff | 23/253 R |
| 3,725,004 | 4/1973 | Johnson | 23/230 B |
| 3,791,930 | 2/1974 | Saxholm | 23/230 B X |
| 3,843,450 | 10/1974 | Saxholm | 23/230 B X |
| 3,853,467 | 12/1974 | Giaever | 23/230 B |
| 3,905,767 | 9/1975 | Morris | 23/230 B |

OTHER PUBLICATIONS

A. Rothen et al., Helvetica Chimica Acta, 54, pp. 1208–1217, (1971).

*Primary Examiner*—Morris C. Wolk
*Assistant Examiner*—Sidney Marantz
*Attorney, Agent, or Firm*—Leo I. MaLossi; Joseph T. Cohen; Jerome C. Squillaro

[57] ABSTRACT

A thin layer of gel on a metallized solid surface has two or more wells formed through the gel which are subsequently filled with specimens of first and second solutions suspected of respectively containing first and second immunologically reactive biological particles specific to each other. The specmens are allowed to diffuse in the gel, and presence of the first and second biological particles in the solutions forms a complexed protein precipitate line on the metallized solid surface corresponding to the region of intersection of the two diffused specimens and which is visible with good contrast to the unaided eye without the need for staining the gel and provides a durable record of the immunological reaction which forms the precipitate.

29 Claims, 8 Drawing Figures

METHOD AND APPARATUS FOR DETECTING IMMUNOLOGIC REACTIONS BY DIFFUSION IN GEL

My invention relates to a method and apparatus for detecting an immunological reaction on a solid surface with the unaided eye and obtaining a durable record thereof, and in particular, for detecting the reaction as the result of a double diffusion in a layer of gel on a metallized solid surface and without requiring a staining process.

This application is related to my concurrently filed applications Ser. No. 457,094 entitled "Method and Apparatus for Detecting Immunologically Reactive Biological Particles," Ser. No. 457,092 entitled "Method and Apparatus for Determination of Concentration of Immunologically Reactive Biological Particles," and Ser. No. 457,091 entitled "Method and Apparatus for Quantitative Surface Inhibition Test" as well as to my co-pending applications Ser. No. 266,278 entitled "Method and Apparatus for Detection and Purification of Proteins and Antibodies" filed June 26, 1972, now abandoned, Ser. No. 384,113 entitled "Improved Method and Apparatus for Detection and Purification of Proteins and Antibodies" filed July 30, 1973, now abandoned, and Ser. No. 445,204 entitled "Improved Substrate for Immunological Tests and Method of Fabrication Thereof" filed Feb. 25, 1974, and assigned as herein.

Immunological reactions are highly specific biochemical reactions in which a first immunologically reactive biological particle (generally a protein) known as the antigen, combines (links) with a second protein specific to the antigen, and known as the antibody, to form an immunologically complexed protein. Immunological reactions taking place within a biological system, such as an animal or human being, are vital in combatting disease. In a biological system, the entry of a foreign protein, i.e., the antigen, causes the biological system to produce the specific antibody proteins to the antigen in a process not fully understood at this time. The antibody protein molecules have available chemical combining or binding sites which complement those of the antigen molecule so that the antigen and antibody link or bond to form an immunologically complexed protein.

Most antigens are proteins or contain proteins as an essential part, whereas all antibodies are proteins. Proteins are large molecules of high molecular weight, i.e., are polymers consisting of chains of variable numbers of amino acids. The above-cited co-pending applications disclose that an arbitrary protein will adhere to a substrate in a monomolecular layer only, and that no other arbitrary protein will adhere to the protein layer. On the other hand, the specifically reacting protein to the first protein adsorbed onto the substrate will immunologically bond thereto. In accordance with the teachings of those applications, this discovery is exploited to provide medical diagnostic apparatus in which a slide having a monomolecular layer of one protein adsorbed thereon is used to test suspected solutions for the presence of the specifically reacting protein thereto. If the specifically reacting protein is present in the solution, the slide after exposure to the solution has a bimolecular protein layer thereon. If the specifically reacting protein be absent from the solution, the slide after exposure to the solution has only the original monomolecular layer thereon. Optical, electrical and chemical means for distinguishing between bimolecular and monomolecular biological particle layers are taught in the related co-pending applications and have different degrees of sensitivity and economy.

Because antibodies are produced by biological systems in response to invasions thereof by foreign proteins, the detection of antibodies in a biological system is of medical diagnostic value in determining the antigens to which the system has been exposed. A typical example of diagnostic detection of antibodies is the detection of antibodies to syphilis or gonorrhea in human serum. Conversely, the detection of certain antigens in a biological system also has medical diagnostic value; examples of diagnostic detection of antigens include detection of HCG-protein molecules in urine as a test for pregnancy, and detection of hepatitis-associated-antigen (HAA) molecules in the blood of prospective blood donors.

In order to perform such diagnostic tests, the appropriate protein of the immunologically reacting pair must be obtained. The only known source of an antibody protein is a living biological system. More particularly, onl vertebrates are known at this time to exhibit immunological reactions to the introduction of a foreign protein. For example, many antibodies are found in the blood serum of animals and human beings which have been exposed to the corresponding antigens. Many antigens, however, may be controllably produced in laboratory cultures. However, some antigens, for example, hepatitis-associated-antigens, are at present, like antibodies, only obtainable from the higher living biological systems.

It is known in the immunological art that antibody molecules function as antigens when introduced into the system of a vertebrate to whom they are foreign proteins. Accordingly, specifically reacting antibodies to a given antibody may be readily produced in such vertebrate system.

Double diffusion immunological experiments have been carried out in the prior art in gel in which specimens containing antigens and their antibodies are applied to different wells in the gel and diffuse toward each other to form a complexed protein precipitate line in the gel. This prior art technique is generally known as the Ouchterlony technique. However, the precipitate formed in the gel is only a temporary record of the immunologic reaction since the gel soon deteriorates through normal drying out (desiccates) due to high water content. A further disadvantage of the gel being used as the immunologic reaction medium is that undesired bacteria growth readily develops in the gel during the time it is stored in a suitable environment which would otherwise prevent the deterioration of the gel. Finally, the sensitivity of the immunological experiments in the gel is relatively low and the precipitate line is often not visible to the unaided eye until the gel is suitably stained with a protein material such as Amido Black as described in the book "Methods in Immunology and Immunochemistry", Vol. III, edited by C. A. Williams and M. V. Chase, Academic Press, pages 153 and 169. This staining process adds another step in the method for detecting such immunologic reaction. Also as noted on page 151 in the above-identified book. "It is important to have the bottoms of the wells completely sealed with agar to prevent leakage of antigen or antibody between the gel and surface of the plate."

Finally, although the substrates (slides) described in my hereinabove-referenced patent applications are satisfactory in their performance for detecting a bimolecular layer of immunologically reactive biological particles, such substrates are not, by themselves, well adapted for the double diffusion technique described hereinabove. This result also occurs with another type of metallized slide known in the prior art, the anodized tantalum slide described in the articles "Interactions Among Human Blood Proteins at Interfaces," authors L. Vromane et al., Federation Proceedings, Vol. 30, No. 5 (September-October, 1971) pages 1494–1502 and "Three Simple Ways to Detect Antibody-Antigen Complex on Flat Surfaces", authors A.L. Adams et al., Journal of Immunological Methods 3 (1973) pages 227–232, which is, however, less sensitive than my indium-gold alloy, indium oxide slide disclosed and claimed in my above-referenced co-pending application Ser. No. 445,204, especially in the detection of hepatitis. Another article related to prior art metallized slides is "Immunologic and Enzymatic Reactions Carried Out at a Solid-Liquid Interface," by Alexandre Rothen, Physiological Chemistry and Physics 5, (1973) pages 243–258.

Therefore, a principal object of my invention is to provide an improved method and apparatus for the double diffusion detection of immunological reactions utilizing a gel as the diffusing medium.

Another object of my invention is to provide a simple method and appartus for detecting immunologically reactive biological particles by a double diffusion process without the need for staining the gel in which specimens containing the particles diffuse.

A further object of my invention is to provide a simple method and apparatus for producing a durable record of the precipitate line formed by immunological reaction between the particles which is visible to the unaided eye with good contrast.

Briefly, and in accordance with the objects of my invention, I provide a method and apparatus for detecting second immunologically reactive biological particles in a test solution by direct visual observation of a complexed protein precipitate line formed on a metallized solid surface as the result of an immunological reaction. The metallized solid surface is initially covered with a very thin layer of gel and two or more wells are formed completely through the gel. Then, a specimen of a first solution containing first immunologically reactive biological particles is deposited in a first of the wells, and a specimen of a test solution suspected of containing second biological particles which are specific to the first particles is deposited in a second well spaced from the first, and the two specimens are allowed to diffuse. During the diffusion process, the biological particles permeate the gel and a complexed protein precipitate line forms at the intersection of the diffusing first and second biological particles. The precipitate line is visible with good contrast to the unaided eye without requiring the use of a staining material and forms a durable record of the detected reaction. The apparatus of the metallized solid surface and gel layer is maintained in a moist chamber during the diffusion process and obtains the detection of the second biological particles with a sensitivity substantially better than that which can be obtained with the conventional double diffusion in gel technique. The metallized solid surface can be that of a metallized slide or the surface of a metallized glass or plastic dish as typical examples.

The features of my invention which I desire to protect herein are pointed out with particularity in the appended claims. The invention itself, however, both as to its organization and method of operation together with further objects and advantages thereof, may best be understood by reference to the following description taken in connection with the accompanying schematic drawings wherein:

Figure 1A:
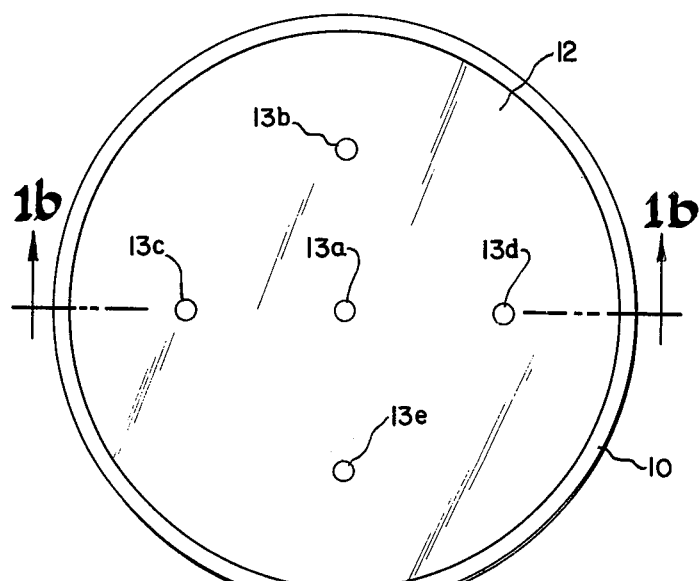
FIG. 1a is a plan view of a metallized dish-gel layer apparatus in accordance with my invention prior to depositing specimens into the wells formed through the gel layer.
Figure 1B:
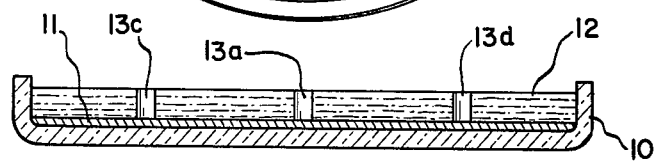
FIG. 1b is an elevation view, in section, of the apparatus illustrated in FIG. 1a taken along line 1b—1b.

Referring now to FIGS. 1a and 1b, there are shown the apparatus, in accordance with my invention, for detecting immunologically reactive biological particles as a result of an immunological reaction thereof occurring on a metallized solid surface. In particular, this first embodiment of my apparatus consists of a suitable container 10 such as a small glass, metal or plastic dish or tray or other type container fabricated of a suitable solid material and having a generally vertically extending lip portion for containing a liquid medium within the container. Metal particles are evaporated on the inner bottom surface of container 10 to form a non-continuous layer 11 of such metal particles to thereby provide a metallized surface on the inside of container member 10. A typical example of the metallization of container 10 is a non-continuous layer of indium globules of average thickness in the order of 2000 to 4000 Angstrom. Alternatively, a continuous film of a single metal, alloy of two metals, or a single metal or alloy of two metals with an oxide film of one of such metals may also be utilized for the metallization of the surface of container 10. The criteria is that a solid surface of some type member on which a very thin layer of gel can be formed is metallized for purposes of improving the sensitivity of my apparatus in the detection of an immunological reaction precipitate line which is subsequently formed on the metallized surface so that the precipitate line is capable of being observed with the unaided eye with good contrast and without the need for staining the gel as is often done in the prior art double diffusion in gel immunological test apparatus. As an example of the aloy metallization, a convenient alloy is that of indium and gold. A typical example of single metal and oxide metallization is indium with an indium oxide film of a few hundred Angstrom thickness, or nickel-nickel oxide. Finally, a typical metallization of an alloy of two metals and oxide film of one of the metals is a gold-indium alloy and indium oxide film wherein such metallization is developed from a continuous or non-continuous layer of indium particles as described and claimed in my above-identified co-pending patent application Ser. No. 445,204.

The metallized container 10 is then placed on a suitable support and a small quantity of gel is poured into container 10 sufficient for covering the metallized surface thereof to a depth less than one millimeter. The most common gels suitable for the immunologic reaction tests are agar and agarose. The gel solution that is poured into container 10 may be a salt solution, distilled water solution or buffered solution thereof depending upon the biological particle solutions to be utilized in the test as described on pages 147 and 148 of the above-referenced book "Methods in Immunology and Immunochemistry." After the gel has solidified, a plurality of closely spaced wells 13a–e are formed through the thin layer 12 of gel in any convenient manner such as described on page 149 of the above-referenced book. The major distinctions between my invention and the prior art diffusion in gel apparatus as described in the above-referenced book are:

1. My apparatus requires a metallized solid surface since the visible precipitate line resulting from an immunological reaction of biological particles is formed on the metallized surface (although the precipitate line is also formed in the gel). In the prior art apparatus no metallized solid surface is required although a means for merely supporting the gel layer is used.

2. My gel layer is substantially thinner than the prior art gel layer which is of at least 1 mm thickness and is described in the above-referenced book as being in the range of 1–3 mm. This significant change in thickness results from the fact that in my apparatus the gel is utilized merely as a diffusion medium, i.e., for purposes of holding moisture in an immobile state so that specimens of immunologically reactive biological particles can diffuse along the metallized-solid-surface to form reproducible precipitate lines thereon. In the prior art apparatus the precipitate line is formed in the gel and therefore requires a thicker layer of gel in order to form a sufficiently thick precipitate line to make it visible.

3. As a result of (2) the precipitate line formed with my invention becomes a durable, and can be a permanent, record of the immunologic reaction, and requires no staining to be visible. In the prior art apparatus the gel often requires staining in order for the precipitate line to be visible (with much less contrast than in my invention) to the unaided eye.

4. In my invention the wells are formed completely through the gel layer. In the prior art apparatus as noted on page 151 in the above-referenced book, the bottoms of the wells must be sealed from the surface of a plate on which the gel is supported. Although my apparatus operates satisfactorily with the bottom of the wells also being sealed from the metallized surface of container 10, such sealing of the bottom of the wells is not necessary, and it is preferred to form the wells completely through the layer of gel as indicated in all of my figures. This significant distinction between the wells results from the fact that the visible precipitate line in my apparatus is formed on a metallized solid surface whereas in the prior art it is formed within the gel itself.

The wells 13a–3 formed through gel layer 12 are generally circular in cross section and are generally of equal diameter as small as one millimeter and as large as several millimeters. My apparatus just prior to the specimens of immunologically reactive biological particles being deposited into the wells is as shown in FIGS. 1a and 1b.

Figure 2A:
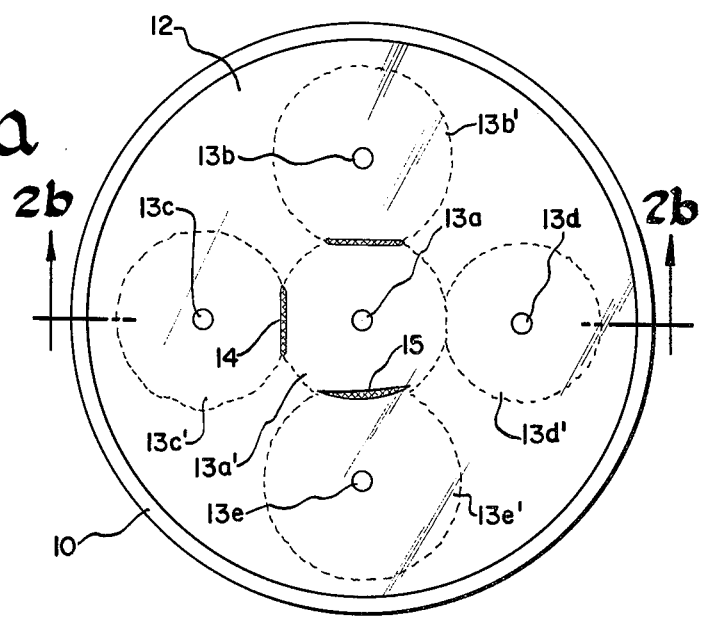
FIG. 2a is a plan view of the apparatus of FIG. 1a after diffusion of the specimens and formation of precipitate lines.
Figure 2B:
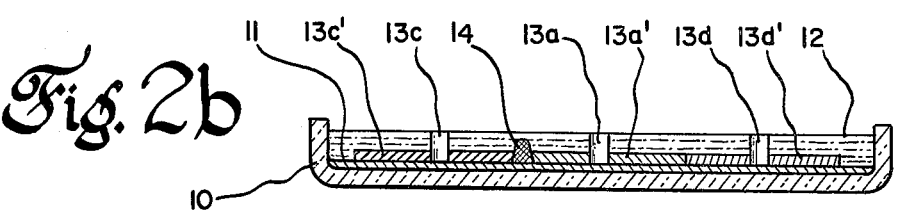
FIG. 2b is an elevation view, in section, of the apparatus illustrated in FIG. 2a taken along line 2—2b.

The gel covered metallized solid surface assembly is then placed in a moist chamber to prevent dessication of the gel and a specimen of a first solution containing first immunologically reactive biological particles is deposited in a first well, for example, centrally located well 13a. Each of the specimens described herein may consist of one or more drops of the corresponding solution. Immediately after the first specimen is deposited in well 13a, or at the same time, a specimen of a first test solution suspected of containing second immunologically reactive biological particles which are specific to the first particles is deposited in well 13c and the two specimens are allowed to diffuse in the gel. The first and test solutions generally also contain other (nonspecific) biological particles, a typical example being a first solution of rabbit anti-serum and a test solution of human serum. During the diffusion of the two specimens in the gel, the first and other (nonspecific) biological particles in the first specimen permeate the gel and are adsorbed onto the metallized solid surface to form a monomolecular layer $13a'$ thereof as illustrated in FIGS. 2a and 2b. In like manner, presence of the second particles in the first test specimen results in the second and other (nonspecific) biological particles permeating the gel and being adsorbed onto the metallized solid surface to form a monomolecular layer $13c'$ thereof. Along the region of intersection of the two diffusing specimens there is formed a complexed protein precipitate line 14 which is several layers thick and results from an immunologic reaction of the first and second particles. The specimens diffuse in the gel radially outward from the wells to form circular patterns such that precipitate line 14 is a straight or curved line depending on the types of particles and concentrations thereof. The time for completion of the diffusion and formation of the precipitate line is a function of the types of first and second particles involved, the concentrations of each particle in its respective solution, the temperature and the spacing of the wells in the gel. Thus, a close spacing of the wells results in the diffusing particles intersecting more rapidly and thereby forming the precipitate line 14 more rapidly than if the wells were spaced further apart. The wells may be spaced apart as little as several millimeters. The time for diffusion of the specimens in the gel and formation of the precipitate line is generally several hours, although the process can be speeded up to several mintures if electrophoresis is employed. Since the moisture is held immobile in the gel, a controlled diffusion of the specimen occurs in the gel to thereby obtain reproducible results.

After formation of precipitate line 14 on the metallized surface of solid member 10, the layer 12 of gel is peeled or otherwise removed from the metallized solid surface. The metallized surface with the precipitate line 14 adhered thereon is then rinsed, typically with distilled water and dried preferably by blowing air at room temperature across the metallized solid surface. The metallized solid surface is then visually examined by direct visual observation in that the unaided eye is employed to observe the light reflected off or transmitted through the metallized surface. The indium particle slide is viewed by transmitted light whereas the indium-gold alloy, indium oxide slide is viewed by reflected light. The color of the precipitate depends primarily on the color of the metallized surface.

The complexed protein precipitate line 14 is visible with good contrast to the unaided eye. A smaller amount of the biological particles is needed to obtain a visually detected precipitate line on the metallized solid surface as compared to the amount of particles needed to form such precipitate line in the gel in the prior art. Thus, my invention results in the detection of immunologic reactions and the biological particles involved therein to a sensitivity which is considerably better than that obtained with conventional double diffusion in gel techniques. Finally, no staining of the precipitate is required, as distinguished from the prior art double diffusion techniques in order to visually detect the precipitate line, and the contrast is also significantly better than that obtained with the prior art techniques.

In the detection method described hereinabove, it was assumed that the first solution was a known solution containing the first biological particles. Alternatively, both the first and second solutions may be test solutions suspected of containing the first and second particles in which case formation of the precipitate line would indicate that such particles were, indeed, contained within the respective solutions whereas absence of the precipitate line would merely indicate that one or both of the solutions did not contain their respective particles. In the case of the known solution containing the first particles, such first particles may be produced in laboratory cultures or obtained from the higher living biological systems as described hereinabove, and are commercially available in highly purified form, and if not available commercially, may be purified chemically. A typical solution of the first biological particles may be a salt solution of water or other liquid appropriate to, and not reactive with, the first biological particles, or a human serum sample.

The biological particles referred to hereinabove as first and second biological particles may be anitgens, antibodies, viruses, bacteria, hormones, enzymes or other biological particles which can be readily grown or otherwise isolated and collected or are present in human serum or other solution being tested. A typical example of particular biological particles which are detected by the method and in the apparatus described hereinabove is hepatitis B antigen (HBA$g$) as the first biological particles and antibodies to hepatitis (HBA$b$) as the second biological particles.

In many cases, the specimen of first particles will be a specimen containing the particular antigens such as HBA$g$. In such case, the test solution would be a drop of human serum taken from a patient suspected of having had hepatitis B, and in a direct test therefore, the presence of antibodies (HBA$b$) would be detected by direct visual observance of precipitate line 14. Alternatively, the particles in the first specimen can be antibodies to a particular disease, and in a direct test, the presence of antigens to such antibodies in the serum sample would be determined by my detection test.

An indirect or inhibition test for the detection of particular immunologically reactive biological particles may also be conducted with my apparatus. The principle of the inhibition test is that the first particles, if present in sufficient quantity, will neutralize free second particles in solution. Thus, in the inhibition test, HBA$g$ particles, if present in sufficient quantity, will neutralize free antibodies to hepatitis B in solution. This reaction will prevent the antibodies from forming observable complexes with HBA$g$ when the test specimen is deposited in well 13$b$ in gel layer 12.

The inhibition test for an antigen, and specifically HBA$g$ is accomplished as follows: A specimen of known solution of HBA$g$ is deposited in well 13$a$ of gel layer 12 and the HBA$g$ and other particles present in the solution are adsorbed as a monomolecular layer 13$a$ on the metallized surface of solid member 10 as in the direct test described hereinabove. The test solution is prepared by adding a human serum sample to be tested to a solution of HBA$b$ in a vial or other suitable container. The vial is then stored for a time interval sufficient for the HBA$b$ to complex with HBA$g$ in the human serum sample, if the antigen is present therein. The vial is preferably agitated to increase the rate of complexing. Finally, a specimen of the test solution is deposited in well 13$c$ of gel layer 12, and after a suitable period of time for the diffusion of the specimens, gel layer 12 is peeled from solid member 10 and the metallized surface of member 10 is visually examined. The results of the inhibition test are the opposite of the direct test, that is, presence of HBA$g$ in the human serum sample produces no precipitate line 14 whereas presence of such precipitate line indicates absence of HBA$g$ in the human serum sample.

The inhibition test for the detection of HBA$b$ is performed similarly to the inhibition test for HBA$g$ with the obvious substitution of the antigen for antibody and antibody for antigen in each of the steps.

In the above hepatitis tests, the HBA$b$ may be obtained from human serum of a patient known to have had hepatitis B, or it may be developed in a goat, rabbit or other suitable animal by injection thereof with the HBA$g$, waiting a suitable incubation period such as two weeks, and then drawing blood containing the specific antibody from the animal and separating the antibody from the remaining blood particles.

In the case where the first solution is known to contain the first biological particles, the specimen of such first solution is deposited in centrally located well 13$a$, and specimens of various test solutions suspected of containing the second biological particles are deposited into the surrounding wells 13$b$, $c$, $d$, and $e$. In each case of sufficient concentration of the second particles in the corresponding test solution, a straight or curved precipitate line is formed at the intersection of the outwardly diffusing first and second immunologically reactive biological particles, and is a detection test for the presence of the second biological particles in the test solutions. Thus, as depicted in FIGS. 2$a$ and 2$b$, specimens of three different test solutions deposited into wells 13$b$, $c$ and $e$ contain the second particles due to the formation of the illustrated precipitate lines whereas the specimen of a fourth test solution deposited into well 13$d$ either did not contain the second particles, or contained it in too dilute a quantity to be detected. In the case where the first solution is known to contain the first biological particles, and one of the other solutions contains a known concentration of the second particles, a specimen of the first solution is deposited into centrally located well 13$a$ and a specimen of the "standard solution" (known concentration of second particles) is deposited into one of the surrounding wells, say well 13$c$. The relative position of the precipitate line 14 formed on the metallized solid surface between wells 13$a$ and 13$c$ is then the standard against which the relative positions of any other precipitate lines, formed as the result of specimens of test solutions suspected of containing the second biological particles being deposited in the other surrounding wells 13$b$, 13$d$, 13$e$, are compared in order to determine the concentration of the second particles in such test solutions. Thus, since the position of precipitate line 15 between 13$a$ and 13$e$ wells is closer to well 13$a$ than is the "standard" precipitate line 14, this indicates that the concentration of the second particles in the specimen deposited into well 13e is greater than the "standard" concentration. In this latter (concentration) test, the surrounding wells are equi-distant from central well 13a.

Figure 3A:
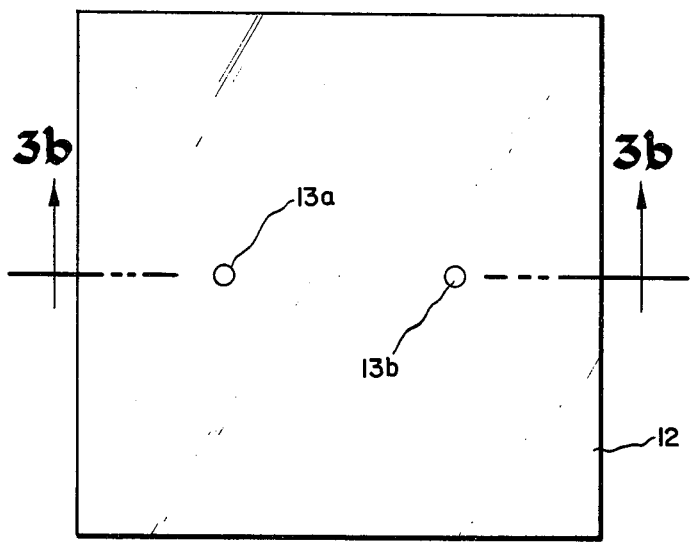
FIG. 3a is a plan view of a metallized substrate-gel layer apparatus in accordance with my invention prior to depositing the specimens into the wells formed through the gel layer.
Figure 3B:
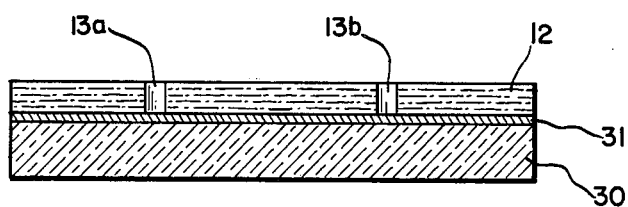
FIG. 3b is an elevation view, in section, of the apparatus illustrated in FIG. 3a taken along line 3b—3b.
Figure 4A:
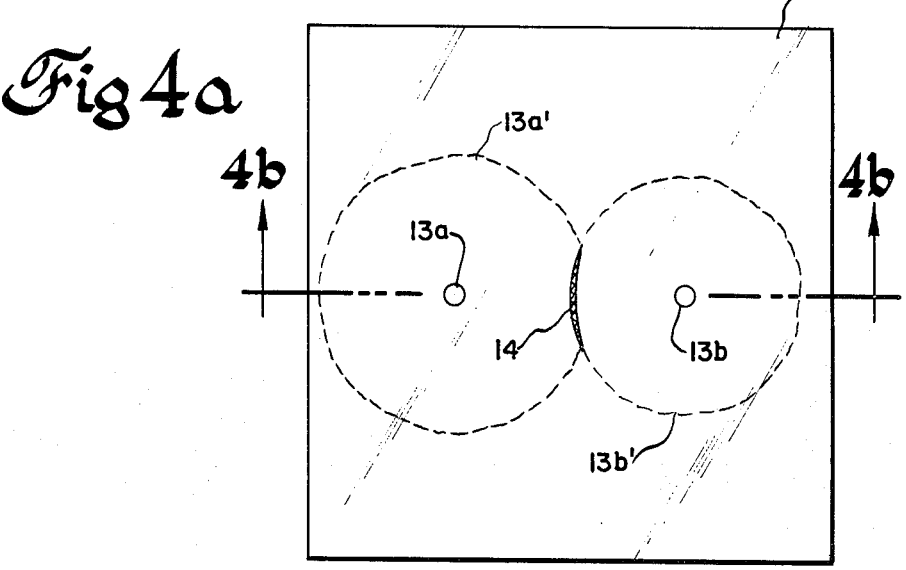
FIG. 4a is a plan view of the apparatus of FIG. 3a after diffusion of the specimens and formation of the precipitate line.
Figure 4B:
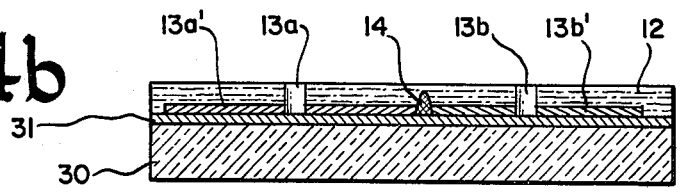
FIG. 4b is an elevation view, in section, of the apparatus illustrated in FIG. 4a taken along line 4b—4b.

Referring now to FIGS. 3a and 3b, there is shown a second embodiment of my apparatus wherein the metallized solid surface member is now a metallized substrate or slide of the type described in my above-referenced co-pending application Ser. No. 445,204. In particular, substrate 30 has a substantially flat top surface and is fabricated of a suitable material which may be a metal, glass, plastic, or similar material. Substrate 30 is preferably in the form of a glass slide such as a conventional microscope cover glass that is readily commercially available. The top flat surface of substrate 30 is metallized in accordance with the teachings disclosed in my above-identified patent applications which are hereby incorporated by reference herein. As examples of such teachings, the metallization may consist of (1) a non-continuous layer, i.e., metal particles or globules with indium being a typical metal, or (2) a first layer of the indium globules overlayed with a thin gold film, or (3) a layer of the indium globules (or a constant thickness continuous layer of indium) overlayed with a thin film of gold which is alloyed with the indium and a thin oxide film of the indium or (4) a metal such as nickel and oxide film thereof. The indium particle metallization is often the preferred embodiment for generally equal size particles whereas the indium-gold alloy and indium oxide coated substrate is often the preferred embodiment for very differently sized particles such as when testing for hepatitis. Following the teaching of the above-referenced patent applications, the non-continuous layer of indium particle metallization requires use of a light-transmissive substrate material such as glass or plastic, and the indium particles evaporated on the substrate surface have diameters on the order of 1000 Angstrom although the precise size of the particles is not critical as long as they have diameters equal to a large fraction of a wavelength of visible light. The color of the indium particle metallization is a light brown. In the case of the indium-gold alloy, indium oxide metallization, the thickness of the indium is approximately twice the thickness of the gold when initially deposited (indium thickness is approximately 2000 A, gold is approximately 1000 A) and the indium oxide film is several hundred Angstrom to obtain a bronze color of such film. As noted in my patent application Ser. No. 445,204 the degree of oxidation of the indium metal determines the color of the oxidized film so that various degrees of oxidation produce different colored slides having different sensitivities for different thicknesses of the layers of the biological particles.

In the case of the metallized coating 31 on the top surface of substrate 30 being formed of globules alone or globules of a first metal such as indium, a film of a second metal such as gold and the oxide film of indium, the top surface of such metallized coating is slightly irregular. Alternatively, such metallized coating when formed with a continuous, constant thickness layer of the indium, film of gold and the indium oxide, has a top surface that is substantially flat. Either type of metallized substrate 30 may be utilized in this second embodiment of my invention. Substrate 30 may be as small as a half inch square. Further details of the substrate metallization and fabrication thereof are disclosed in my above-referenced patent applications which are hereby incorporated by reference herein.

My apparatus employing metallized substrate 30 is fabricated in the same manner as my first embodiment. Thus, a thin layer (less than 1 mm) of gel 12 is formed on the metallized surface of the substrate and two or more wells 13a, 13b are formed, preferably completely through the gel layer. The apparatus is then utilized in the same manner as my first embodiment in that a specimen containing first immunologically reactive biological particles (and other non-specific particles) is deposited into well 13a and a test specimen suspected of containing second (and other nonspecific) immunologically reactive biological particles specific to the first particles is deposited into well 13b. The apparatus is then maintained in a moist chamber for a time interval sufficient for the two specimens to diffuse through the gel so that a monolayer 13a' of the first and other nonspecific particles is adsorbed onto the metallized surface 31 of the substrate and, in a like manner it is evident that a monolayer 13b' of any second and other nonspecific particles is also adsorbed onto the metallized surface and at the intersection of the two diffusing specimens a complexed protein precipitate line 14 is formed which, after removal of the gel layer, is clearly visible to the unaided eye by observing the light reflected off or transmitted through the metallized surface 31. After removal of the gel layer, the precipitate line 14 remains adhered on the metallized surface and again forms a durable record of the immunological reaction between the first and second immunologically reactive biological particles. The complexed protein precipitate line 14 is again several layers thick and is a straight or curved line. After the gel is peeled from the metallized surface of the substrate, such surface is again rinsed with distilled water and dried as in the case of my first embodiment. In the case of the indium particle metallization the precipitate is a much darker shade of brown as compared to the light brown background. In the case of a bronze color indium oxide film as the outermost surface of the metallization layer 31, the precipitate is a purplish line which is clearly distinguished from the bronze color background.

In each of the two embodiments of my invention described hereinabove, it is noted that no staining of the gel is required in order to make visible the precipitate line 14. Also, the greater sensitivity of my apparatus, in that the plurality of layers of biological particles which form the precipitate line 14 are more easily detectable, makes my testing method more sensitive. That is, the precipitate line is more readily visible (for the same amount of biological particles) on the metallized substrate than in the gel, and therefore a smaller amount of such particles can be detected with my apparatus. Since my apparatus is more sensitive than the apparatus used in the Ouchterlony technique, a lesser amount of the first biological particles and smaller specimens of the test solution need be deposited into the wells in the gel layer in my apparatus and therefore an economy in the case of such particles is realized which may be particularly significant in the case where the first particles are obtained from a costly laboratory process, and, or, where the physical condition of the patient is so poor that the taking of a larger specimen from him may be detrimental to his condition. Finally, the precipitate line formed on my metallized solid surface forms a durable and even permanent record of the immunological reaction which is not true in the Ouchterlony technique unless the nonspecific particles are first removed in a water bath requiring approximately 24 hours, then staining the gel, another washing process to remove the stain in the gel material, but not from the precipitate line, and finally drying the gel in a slow delicate process.

From the foregoing description, it can be appreciated that my invention makes available an improved double diffusion method and apparatus for detecting immunologically reactive biological particles in a test solution by direct visual observation of the metallized surface of a solid member on which a complexed protein precipitate is formed as a result of an immunological reaction between first biological particles and the particular biological particles being investigated and which are specific to the first particles. My method and apparatus are very simple in that only a thin layer of gel with suitable wells formed therethrough is required on the metallized solid member for diffusion of the specimens and the unique and highly sensitive properties of the metallized solid member, and in particular the metallized substrate, thereby avoids the need for staining the gel or substrate in order to detect the precipitate line by direct visual observation. As a result, I have provided a simple method wherein the previously described metallized slide described in the hereinabove-referenced patent applications can now be adapted for use with a double diffusion of specimens in a thin gel layer for detecting the biological particles. Since the metallized slides, in particular, can be fabricated repetitively with identical characteristics, the results of the detection of the biological particles in accordance with my present invention are very consistent and can serve many useful purposes, especially in the medical diagnostic field in the analysis of human serum, for example, for the detection of various antibodies and antigens therein. Since the visual contrast between the precipitate line and monomolecular layer of biological particles is very distinct when utilizing my metallized solid surface, the detection is accomplished by direct observation with the unaided eye and therefore does not require elaborate test equipment and obtains the precipitate line in durable form.

Having described my invention with reference to two specific embodiments, it is believed obvious that modification and variation of my invention is possible in the light of the above teachings. Thus, the shape and size of the substrate or solid member and thin layer of gel may be varied and virtually any pair of immunologically reactive biological particles which will immunologically react with each other can be detected with my apparatus. Further, my metallized substrate, if sufficiently large, can be employed to detect the presence of the second biological particles in more than one test solution by depositing the specimens thereof in other wells formed through the thin gel layer surrounding a central well in which the specimen known to contain the first particles is deposited as in the first embodiment illustrated in FIGS. 1a and 2a. The presence of the second particles in each test solution is then detected by observing the formation on the metallized substrate of precipitate lines formed by the first particles in the central diffusion immunologically reacting with the second particles in the respective intersecting surrounding diffusions. A measure of the concentration of the second particles in the test solutions can also be obtained in this manner if one of the second solutions (i.e., a standard solution) contains a known concentration of the second particles. A good approximation of the concentration can be estimated by comparing the relative position of each precipitate line (relative to the distance between the wells in which the first particle specimen and each test solution specimen is deposited) to that of the relative position of the precipitate line formed by the standard solution specimen. Further, metallizations other than the indium and indium-gold alloy, indium oxide may be found to obtain better contrast of the precipitate line on the metallized surface for some specific biological particles. Also the irregular surface embodiment of my metallized slide could obviously also be fabricated by starting with an irregular surfaced substrate and evaporating constant thickness layers of a metal such as indium thereon. Finally, it should be evident that my apparatus may also be utilized for determining the concentration of the second biological particles by first adsorbing a monomolecular layer of the first biological particles along substantially the entire metallized surface of the solid member 10 or substrate 30, and then forming the thin gel layer 12 on top of the first particle layer in complete contact therewith. The specimen of the test solution is then deposited into a well formed in the gel layer, and diffusion of such specimen results in an immunologic reaction whereby a monomolecular layer of only the second biological particles is formed on top of the first particle layer in the shape of a small circular spot if the test solution contains such second particles. The diameter of the second layer spot, which is visible with good contrast to the unaided eye as a purplish spot in the case of a bronze color metallized slide, is related to the concentration of the second particles in the test solution. Thus, in the conduct of this variant method coating 31 on substrate 30 would represent both the metallization layer and monomolecular layer of first biological particles. A specimen of a first test solution is then deposited into well 13a and a specimen of a second test solution, or a standard solution (i.e., solution of known concentration of the second particles) is deposited into well 13b, and 13a', 13b' are the circular spot monomolecular layers of the second particles. Thus, my apparatus as fabricated may also consist of a metallized substrate with a monomolecular layer of first immunologically reactive biological particles that adhere thereto and a thin layer of gel disposed thereon. After formation of the second layer spot(s) the gel layer is removed, the metallized slide is rinsed, dried, and then visually examined with the unaided eye and the diameter(s) (or areas) of the second layer spot(s) is measured (and compared to a standard) for determining the second particle concentration. It is, therefore, to be understood that changes may be made in the particular embodiment of my invention as described which are within the full intended scope of the invention as defined by the following claims.

What I claim as new and desire to secure by Letters Patent of the United States is:

1. Apparatus for determining the presence or absence of select biological particles in a biological sample, comprising in combination
a solid substrate member having a metallized surface area thereon and
a gel layer on and in direct contact with said metallized surface area, said gel layer having a plurality of holes therethrough exposing metallized surface area at the bottom of said holes, said gel layer being substantially free of biological particles.

2. The apparatus set forth in claim 1 wherein the solid substrate member is formed of a light-transmissive material selected from the group consisting of plastic and glass.

3. The apparatus set forth in claim 1 wherein the metallized surface of the solid member is a non-continuous film consisting of metal particles.

4. The apparatus set forth in claim 1 wherein the metallized surface of the solid substrate member is formed of a metal and an outer film of an oxide of the metal.

5. The apparatus set forth in claim 1 wherein the metallized surface of the solid substrate member is formed from an alloy of two metals.

6. The apparatus set forth in claim 1 wherein the holes through the layer of gel are spaced apart in the order of several millimeters.

7. The apparatus set forth in claim 1 wherein the material of the gel layer is agar.

8. The apparatus set forth in claim 1 wherein the thickness of the gel layer is less than 1 millimeter.

9. The apparatus recited in claim 1 wherein the gel yer is formed from an aqueous liquid.

10. The apparatus recited in claim 9 wherein the queous liquid is distilled water.

11. The apparatus set forth in claim 1 wherein said solid substrate member is a container, the inner bottom surface of said container having the metallized surface area.

12. The apparatus set forth in claim 11 wherein the container is a dish-shaped member.

13. The apparatus set forth in claim 11 wherein the container is formed of metal.

14. The apparatus set forth in claim 1 wherein the metallized surface of the solid substrate member is formed from an alloy of two metals, and has oxide of one of the two metals therein.

15. The apparatus set forth in claim 14 wherein the two metals are indium and gold and the oxide is indium oxide.

16. The apparatus set forth in claim 15 wherein the surface of the solid substrate member beneath the metallized surface area is flat and the metallized surface area is slightly irregular.

17. The apparatus set forth in claim 15 wherein the surface of the solid substrate member beneath the metallized surface area is flat and the metallized surface area is flat.

18. A method for determining the presence or absence of select biological particles in a biological sample, comprising the steps of:
disposing a gel layer on and in direct contact with a metallized surface, said gel layer having a plurality of spaced holes therethrough and being substantially free of biological particles,
placing a quantity of solution containing biological particles specific to said select biological particles in a first of said holes,
placing a quantity of biological sample in a second of said holes,
preventing desiccation of said gel layer during diffusion of said quantities of solution and biological sample through gel material adjacent said metallized surface,
removing said gel layer and
inspecting the exposed surface to determine the presence or absence of precipitate line adhered to said metallized surface between positions thereon coinciding with the bottoms of said first and second holes.

19. The method set forth in claim 18 wherein the gel layer disposed on the metallized surface is less than one millimeter in thickness.

20. The method set forth in claim 18 wherein the spacing of the holes is in the order of several millimeters.

21. The method recited in claim 18 wherein the select biological particle is an antigen and the biological particle specific thereto is an antibody.

22. The method recited in claim 18 wherein the metallized surface contains oxide of a metal present in the metallized surface.

23. The method recited in claim 18 wherein the metallized surface is irregular.

24. The method recited in claim 18 wherein the metallized surface is substantially flat.

25. The method recited in claim 18 wherein the inspecting step is conducted by means of light transmitted through the metallized surface.

26. The method recited in claim 18 wherein the gel layer is formed on the metallized surface.

27. The method recited in claim 18 wherein a quantity of a standard solution containing a known concentration of select biological particles therein is placed in a third of the holes to produce a standard precipitate line.

28. The method recited in claim 18 wherein the gel layer is formed from an aqueous liquid.

29. The method recited in claim 28 wherein the aqueous liquid is distilled water.

* * * * *